United States Patent [19]

Azuma et al.

[11] Patent Number: 4,795,613
[45] Date of Patent: Jan. 3, 1989

[54] BIOCHEMICAL ANALYZER

[75] Inventors: Masashi Azuma, Hino; Tuneo Narushima, Akishima; Takashi Ishihara, Tachikawa, all of Japan

[73] Assignee: Konishiroku Photo Industry Co., Ltd., Tokyo, Japan

[21] Appl. No.: 53,548

[22] Filed: May 26, 1987

Related U.S. Application Data

[63] Continuation of Ser. No. 755,363, Jul. 16, 1985, abandoned.

[30] Foreign Application Priority Data

Jul. 17, 1984 [JP] Japan ................... 59-148456

[51] Int. Cl.4 ........................................... G01N 35/04
[52] U.S. Cl. ..................... 422/64; 356/246; 422/67; 436/46
[58] Field of Search ............... 436/44, 46, 47; 422/63-67, 72, 102; 356/244, 418, 445, 246

[56] References Cited

U.S. PATENT DOCUMENTS

| | | | |
|---|---|---|---|
| 4,113,436 | 9/1978 | Werder et al. | 422/67 |
| 4,119,407 | 10/1978 | Goldstein | 422/72 |
| 4,133,642 | 1/1979 | Nosaka et al. | 422/67 |
| 4,224,032 | 9/1980 | Glover et al. | 436/46 |
| 4,226,537 | 10/1980 | Colley | 422/72 |
| 4,279,514 | 7/1981 | Blumel et al. | 356/244 |
| 4,430,299 | 2/1984 | Horne | 422/66 |
| 4,488,810 | 12/1984 | Hatanaka et al. | 422/64 |

FOREIGN PATENT DOCUMENTS 58-156835 9/1983 Japan ..................... 422/64

Primary Examiner—Michael S. Marcus
Attorney, Agent, or Firm—Finnegan, Henderson, Farabow, Garrett & Dunner

[57] ABSTRACT

A biochemical analyzer provided with a disk for engaging and conveying measuring elements and an analyzing method wherein information held by the measuring elements is detected and the engagement and conveyance of these elements can be controlled on the basis of the detected information. The biochemical analyzer is provided with engagement slots for the measuring elements.

6 Claims, 3 Drawing Sheets

BIOCHEMICAL ANALYZER

This application is a continuation of application Ser. No. 755,363, filed July 16, 1985, now abandoned.

BACKGROUND OF THE INVENTION

1. Field of the Invention

This invention relates to a biochemical analyzer and an analyzing method, and particularly it relates to an apparatus for and method of chemical analysis and measurement of a liquid sample by using a measuring element impregnated with a reaction reagent.

2. Description of the Prior Art

Regarding a liquid sample such as blood and serum, in generally, it is often necessary to know the existence of a specific component or the content thereof or the like in said liquid sample, and chemical analysis by using a reaction reagent is conducted for this purpose. There are a dry method and a wet method. According to the dry method, a liquid sample to be analyzed is dripped onto a measuring element which is prepared by putting a thin leaf impregnated with a specified reagent between mounts. The measuring element thus supplied with the liquid sample is set in a thermostatic bath for reaction so as to make the liquid sample and the reagent react on each other, and the state of progress of the reaction or the result thereof is measured and detected, for instance, by a means in which a change in color density due to the reaction is measured by an optical densitometer. This method is very convenient, since it enables the handling of the liquid sample as a solid in practice.

It is troublesome, however, to drip a number of specimens one by one onto the measuring element so as to measure a change in color density due to reactions by the optical densitometer. In this connection, a biochemical analyzer has been developed recently in which a disk enabling the engagement of a plurality of measuring elements at equally-spaced positions on the same circle is provided so that it can be rotated by a prescribed angle so as to move the measuring elements sequentially to a measuring position for photometry. However, the measuring elements require different reaction reagents according to examination items, while necessitating the selection of photometric timing and wavelength of photometric rays of light. Therefore, this apparatus involves very troublesome steps when many kinds of measuring elements being present together on the same disk are treated.

SUMMARY OF THE INVENTION

This invention has been developed for settling the above-described problem, and an object thereof is to furnish a biochemical analyzer which enables the smooth treatment of many kinds of measuring elements being present together on the same disk.

According to the present invention, a biochemical analyzer having a disk for engaging and conveying measuring elements is provided with a detecting means for detecting the information that the measuring elements hold, and is constructed so that said engagement and conveyance can be controlled on the basis of the detecting means so as to enable quick measurement of prescribed examination items, while addresses on the disk, in which measuring elements for any specified examination items, for instance, are positioned, are memorized.

Other objects and characteristics of the present invention will be made clear hereunder with reference to drawings.

DESCRIPTION OF THE PREFERRED EMBODIMENT

The present invention will be described hereunder based on one embodiment shown in the attached drawings.

Figure 4:
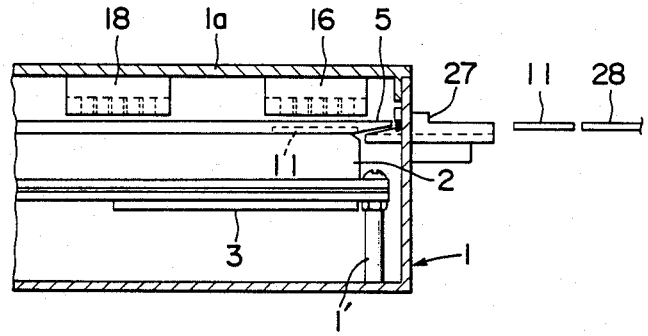
FIG. 4 is a sectional view of an insertion port for the measuring element.

Numeral 1 denotes the main body of a biochemical analyzer (hereinafter called "main body"), and on a base board 1b of the main body 1, a plane circular thermostatic plate 2 is installed through an intermediary of leg members 1', as shown in FIG. 4. The thermostatic plate 2 is made hollow so that a temperature-keeping medium a such as water can be held therein, while it is fitted with an electric heater 3 on the lower surface thereof.

Numeral 4 denotes a rotary shift which is put through a hole 2a piercing the central portion of the thermostatic plate 2, with the upper and lower ends of the shaft supported by a top board 1a and the base board 1b respectively. On the upper portion of the rotary shaft 4 a disk 5 is fitted so that it can move in the axial direction (vertical direction) while fixed in the direction of rotation. The disk 5 is made rotatable in the state that it is set in close contact with or in proximity to the top surface of the thermostatic plate 2 by the pressing forces of a spring 7 put on the rotary shaft 4 and a spring member 8 provided inside with a spring 8" which presses a ball 8' so that it is in contact with the top surface in the peripheral edge portion of the disk 5. It suffices that the spring member 8 is provided in several equally-spaced positions on the circumference of the disk. The rotary shaft 4 is provided with a fan 9 for stirring a heat-keeping medium in the thermostatic plate 2.

Figure 1:
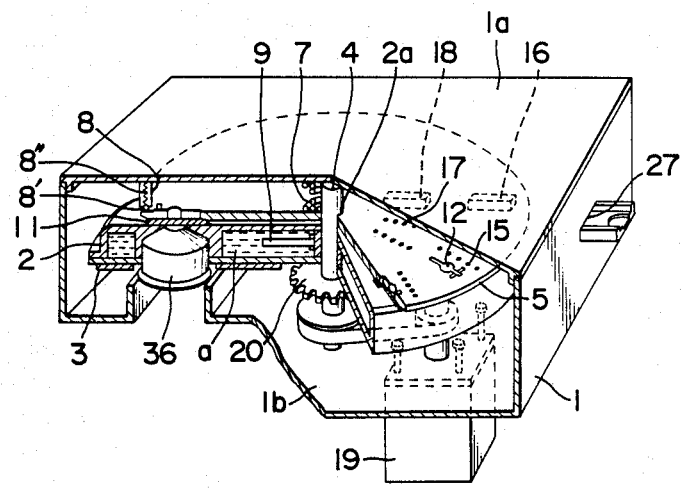
FIG. 1 is a partial cutaway perspective view of an entire apparatus.
Figure 2:
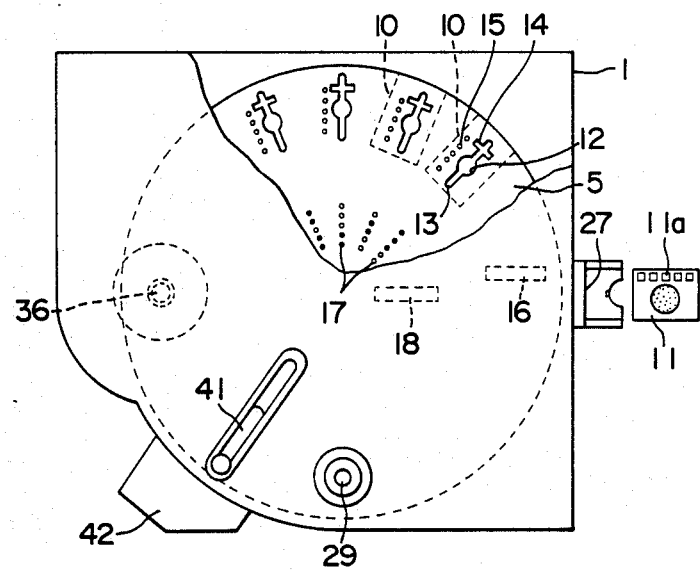
FIG. 2 is a partial cutaway plan view thereof.

Numeral 10, as shown in FIG. 2, denotes an engagement slot which is provided in equally-spaced places on the lower surface of the peripheral edge portion of the disk 5 for engaging a measuring element 11. The height of this engagement slot 10 is made smaller in size than the thickness of the measuring element 11 so that the lower surface of the measuring element 11 engaged therewith can be in sliding contact with the top surface of the thermostatic plate 2 so as to be preheated in conveyance with the rotation of the disk 5. A through hole 12 for pipetting a sample to be examined into the measuring element 11 is provided on the upper side of the disk 5 corresponding to the engagement slot 10.

Figure 3:
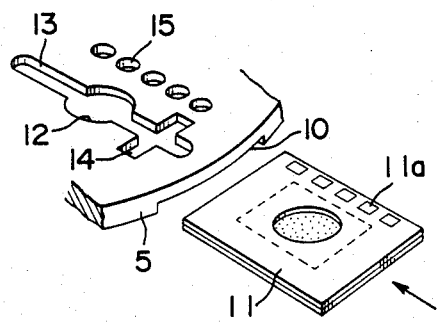
FIG. 3 is a perspective view showing the relationship between a measuring element and an engagement slot thereof.

Numeral 13, shown in FIG. 3, denotes a long hole for discharging the measuring element 11 from the engagement slot 10, and 14, as shown in FIGS. 2 and 3, is a cross-shaped hole for reading identification marks, such as a person's name, entered on the surface of the measuring element 11.

Figure 9:
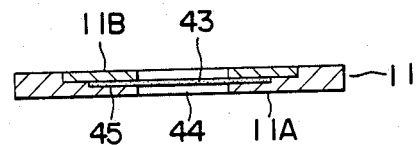
FIG. 9 is a sectional view of the measuring element.
Figure 10:
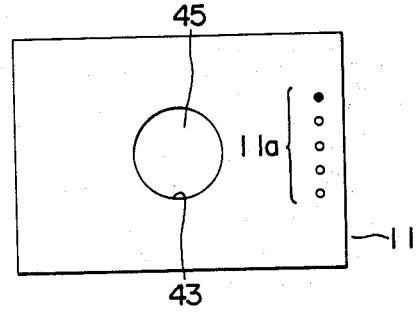
FIG. 10 is a plan view thereof.

As shown in FIGS. 9 and 10, the measuring element 11 is constructed in such a manner that: a monolithic-plate-shaped mount is formed, for instance, from a base 11A of plate-shaped resin and a cover 11B fitted integrally in the base 11A; an analytical membrane 45 impregnated with a chemical analysis reagent is put and held between the base 11A and the cover 11B of the mount; through holes 43 and 44 are formed in the respective centers of the base 11A and cover 11B so as to expose the central portions of the surface and the back of the analytical membrane 45; and a proper coded representation 11a corresponding to the kind of a given chemical analysis element is formed, for instance, in one side edge portion of the mount.

While the aforesaid coded representation 11a may take any form, it is requisite that it can be discerned by a machine, and thus it is preferable that the coded representation is constituted by such a code of arranged white and black dots as illustrated in the figure, a magnetic code marked by magnetic paint or the like, a punch code, a bar code, or the like. Correspondence between some code and some kind of a chemical analysis element may be set quite freely. In addition, while the kind of the chemical analysis element should be assorted in accordance with the kind of a reagent contained in the analytical membrane 42, at least, any codes indicating subdivisions regarding the kind of a liquid sample to be analyzed and any other necessary items may be added.

Since the measuring element of the present embodiment is constructed as described above, the kind of a given measuring element can be ascertained immediately according to the content of the coded representation 11a, so that necessary treatment can be applied thereto, and also the possibility of a mistake or confusion with any other measuring element is eliminated. Accordingly, even when many kinds of measuring elements are made to react in a common thermostatic chamber for reaction, for example, a condition demanded for each measuring element can be secured without causing any false treatment, and consequently the analytical treatment can be performed rapidly without fail.

Moreover, automatic treatment of the measuring element is enabled by making the aforesaid coded representation 11a readable by a machine, and by using a reading machine fitted therefor and a machine for treating the measuring element according to signals sent from the reading machine.

Figure 5:
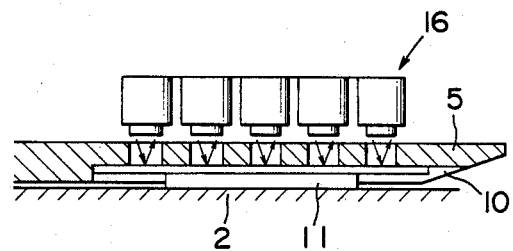
FIG. 5 is a sectional view of a code reading means.

Numeral 15 denotes exposure holes which expose the coded representation 11a for specifying examination items of the measuring element 11, and a means 16 for reading item codes, which is provided on the top board 1a of the main body 1, corresponds to the exposure holes 15. Numeral 17 denotes coded representations for specifying the addresses of the engagement slots which indicate sequential positions of the slots from one engagement slot 10 as a basis, for instance, and these representations are provided radially in the central portion of the top board of the disk 5. A means 18 for reading address codes, which is provided on the top board 1a of the main body 1, corresponds to the coded representations 17. As the detecting devices of the aforesaid reading means 16 and 18, a reflection-type detecting device, as shown in FIG. 5, may be employed, and information detected thereby is stored in a memory (not shown in the figures).

Figure 6:
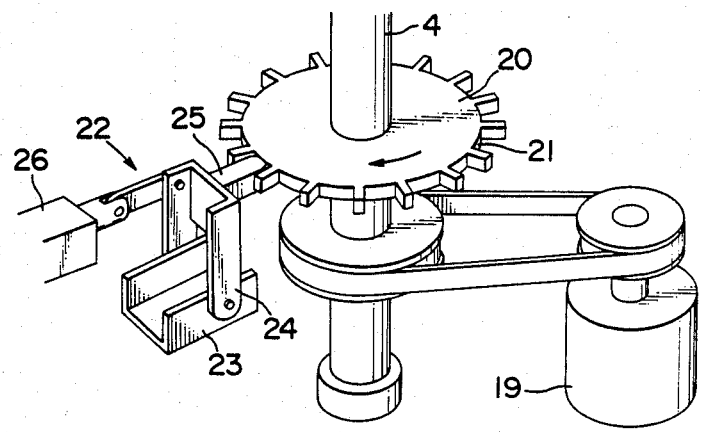
FIG. 6 is a perspective view of a stopper mechanism section.

Numeral 19 denotes a driving source which drives the rotary shaft 4 of the disk 5, and this driving source 19 is connected with the rotary shaft 4 by a belt. 20 denotes a gear-shaped member which has a plurality of grooves 21, as shown in FIG. 6, at the peripheral edge and is fixed to the aforesaid rotary shaft 4. The grooves 21 at the peripheral edge are provided in the same number as the number of engagement slots 10 for the measuring element 11 provided at the peripheral edge of the disks so that they correspond each to one slot, respectively. Number 22, also shown in FIG. 6, denotes a stopper mechanism constructed in such a manner that a tilting member 24 is supported rotatably by a support member 23 fitted on the base board 1b of the main body 1 and a stopper pin 25, whose width is smaller than that of groove 21, is provided on the front side of the tilting member 24. This mechanism is designed so that the stopper pin 25 can be engaged with and disengaged from the groove 21 at the peripheral edge of the gear-shaped member 20 by the operation of a solenoid 26.

Figure 7:
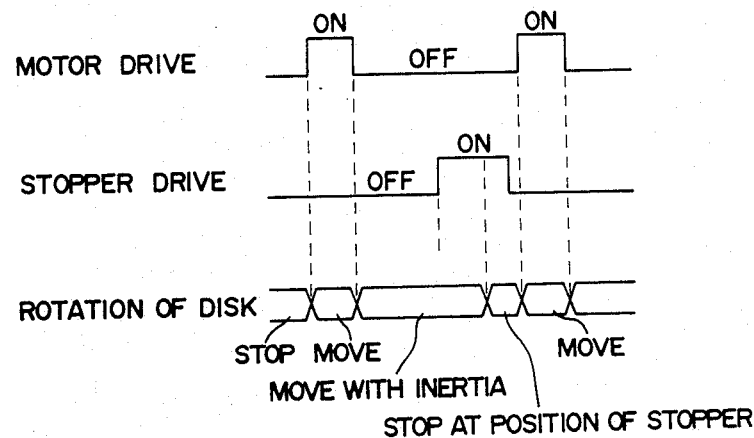
FIG. 7 is a time chart of disk driving and an operation of a stopper mechanism.

When the driving source 19 is turned on, the disk 5 is rotated at a prescribed angle. At this point in time, the driving source 19 is turned off, and simultaneously the solenoid 26 operates to put the stopper pin 25 into the groove 21 so as to stop the disk 5. The timing of operations of the driving source 19 and the stopper mechanism 22 is determined as shown in FIG. 7. In addition, the driving source 19 has a friction mechanism (not shown in the figures) incorporated therein for absorbing the inertia generated when the stopper pin 25 put in the groove 21 contacts with and is stopped by the rear wall of said groove 21.

Numeral 27, shown in FIG. 2 and 4, denotes an insertion port for the measuring element 11, through which the element 11 is inserted into the disk 5. The insertion port 27 is provided in an appropriate place of the side wall of the main body 1 so that it can be aligned with the engagement slot 10 when the disk 5 is stopped. It is preferable that the insertion port 27 be provided with an additional device (not shown in the figures) which can accommodate measuring elements in a stack for every examination item of various kinds and supply a required measuring element selectively to the port, and which is designed so that a measuring element selected can be inserted automatically into the port in linkage to the stoppage of the rotation of the disk 5 by a pusher device 28 (only a pusher plate is shown in the figure).

Numeral 29 denotes a port for pipetting a specimen into the measuring element 11 which engages the engagement slot 10 of the disk 5 and is conveyed thereto over the thermostatic plate 2, and the pipetting port 29 is opened through the top board 1a of the main body 1 corresponding to the position of stoppage of the measuring element 11.

Figure 8:
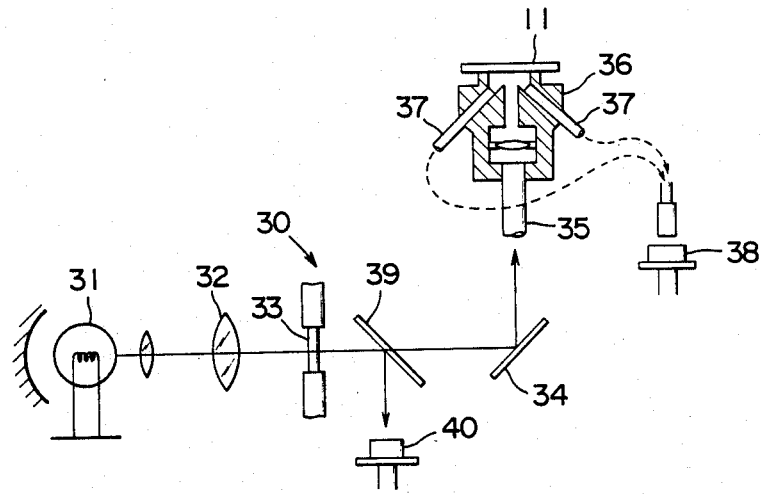
FIG. 8 is a schematic side view of a photometric unit.

Numeral 30, shown in FIG. 8, denotes a photometric unit which measures optically the state of progress or the result of the reaction between the pipetted specimen and the element of the measuring element 11, based on a change in the density of color caused by the reaction. This photometric unit 30 is constructed, as shown in FIG. 8, so that the following process can be performed. A ray of light emitted from a light source 31, such as a halogen lamp, is turned into a photometric ray of a desired wavelength through a lens 32 and a filter 33. The photometric ray is refracted by a mirror 34, guided through an optical fiber 35 and applied onto a photometric head 36 which is provided in proximity to the measuring surface (the back surface) of the measuring element 11. The ray of light applied to the head is reflected from the measuring surface, transmitted to a light-receiving element 38 through optical fibers 37 and subjected to an operation by an arithmetic device (not shown in the figure) such as a computer, and a measured value thus obtained is displayed by a display window (not shown in the figure) which is provided in an appropriate place of the main body 1. This measured value may be printed on rolled recording paper (not shown in the figure) as occasion calls.

In addition, numeral 39 denotes a transparent glass which is provided, with an inclination of 45 degrees, on the optical path of the photometric ray so as to eliminate, as much as possible, an error in the measured value caused by a variation with time of the amount of the photometric ray etc., and a part of the ray, which is reflected by the transparent glass 39, is sent as a reference to a compensation circuit (not shown in the figure) via a light-receiving element 40 so that the measured value of the photometric ray reflected from the measuring element can be compensated to a correct value.

As shown in FIG. 2, numeral 41 denotes a discharging mechanism for discharging the measuring element 11 after measurement is conducted, and 42 denotes a tray for holding discharged measuring elements outside the main body.

Next, a description will be given for the operation of the present apparatus.

First, the disk 5 is rotated through each set angle (one pitch) of the engagement slot 10 and stopped to allow the measuring element 11 to be inserted sequentially into the insertion port 27 thereof. Then, the coded representation 11a marked on the surface of the inserted measuring element, is read by the item code reading means 16 so that the examination item is checked up, while the address of the engagement slot of the disk 5 into which the measuring element of said examination item is inserted is read by the address code reading means 18 and stored in a memory. The storage is made in such a manner that the address of the measuring slot 10 into which a measuring element for examining an item A (an element A) is inserted is stored as "01", for instance, the address of the engagement slot 10 into which a measuring element for examining an item B (an element B) is inserted - as "02", and the address of the engagement slot 10 into which a measuring element for examining an item C (an element C) is inserted - as "03". If the measuring element is inserted erroneously upside-down, the error can be detected.

Next, a specimen to be analyzed by an operator is taken in a pipette from a test tube or the like and injected therefrom into the element passing through the pipetting port 29.

Then, the operator specifies an analysis item by operating an operation board, which is not shown in the figures. When this specification relates to the element B, for instance, the arithmetic device (not shown in the figure) computes how many pitches separate the position of the engagement slot with the element B inserted therein from a basic point, and how many pitches are left to the photometric unit from the position.

Then the driving source 19 of the disk is turned on and the operation is started. When the disk is rotated through a necessary angle, the driving source 19 is turned off and simultaneously the stopper pin 25 is put into the groove 21 to stop the disk 5. Thereby the prescribed measuring element is stopped above the top surface of the photometric head of the photometric unit 30. Here a photometric ray of light from the light source 31 is applied onto the measuring surface, and the ray reflected therefrom is transmitted to the arithmetic device such as a computer through the light-receiving element 38 to be subjected to an operation. A measured value obtained from the operation is displayed in the display window of the main body. This value is recorded simultaneously on rolled recording paper. The same process as described above is performed for other measuring elements.

All the movement of measuring elements can be specified beforehand. When it is specified beforehand by the operator that the photometry be applied to the element A three minutes later, to the element B four and eight minutes later and to the element C fifteen minutes later, for example, the rotation of the disk is controlled so that the position given the address of "01" corresponding to the element A can come to correspond to the photometric position three minutes later, the position given "02" four and eight minutes later, and the position given "03" fifteen minutes later. This control can also be scheduled by the CPU. In case a photometric wavelength of each measuring element is different, each measuring element can be detected by storing each photometric wavelength in the CPU.

After measurement is performed, the measuring elements are discharged, through a discharging mechanism 41, into a holding tray 42 provided outside the main body.

The description of the above embodiment includes an apparatus in which the measuring elements and the disk are provided with coded representations respectively, while the means of reading these coded representations is provided, and thus each coded representation corresponds, one to one, to each engagement slot of the disk. However, the application of the present invention is not limited to this embodiment. Another embodiment may be referred to in this connection, in which an element to be sensed by a sensor is provided at a prescribed position of the disk to be used as a basic position, or an encoder is provided at the disk or a disk-driving system or the like and an encoder pulse from the basic position is made to correspond to the code of a measuring element so that the rotation of the disk can be controlled on the basis of the number of the said encoder pulses when measurement is conducted.

There may be still another embodiment in which all the measuring elements in the required number are set on the disk and then the disk is rotated once to read the examination item codes and the sequence of setting of the measuring elements to be stored. Since the examination item codes of the measuring elements serve as position codes in this embodiment, the rotation of the disk can be controlled on the basis of the examination item codes stored.

Moreover, since examination items are represented by codes in these embodiments, it is advisable to change the type of filter 33 based on the information on the items.

As described above, the present invention includes a biochemical analyzer provided with the disk for engaging and conveying the measuring elements, the means of detecting the information that the measuring elements hold is provided, and the engagement and conveyance of these elements can be controlled on the basis of the detection by said detecting means. Various advantages result from use of the invention because photometric treatment can be performed reliably and uniformly even when many kinds of measuring elements are present together on the same disk.

What is claimed is:

1. A biochemical analyzer comprising:
   a plurality of measuring elements, each containing a respective sample to be tested and information relating to the test to be conducted on said respective sample;
   conveying means for selectively conveying each of said measuring elements to a measurement position, said conveying means including indications specifying the address positions of the measuring elements and a support with a plurality of engagement slot means for holding the measuring elements, said engagement slot means being provided with exposure hole means for exposing said information on the measuring elements, and said support including through hole means for permitting pipetting of said respective samples;
   measuring means for testing each respective sample at said measurement position;
   detecting and reading means for detecting and reading said information relating to the test to be conducted on said respective samples when said detecting and reading means is aligned with said information relating to the test to be conducted and for detecting and reading the corresponding address positions of said respective samples when said detecting and reading means is aligned with said corresponding address positions;
   storage means for receiving and storing said information detected and read by the detecting and reading means relating to the test to be conducted on said respective samples and the corresponding address positions of said respective samples; and
   processing and control means for processing the stored information and responsively controlling said conveying means to selectively convey each measuring element to said measurement position for testing at an appropriate timing and sequence determined based on said stored address positions of said respective sample and based on said stored detected information relating to the test to be conducted on said respective samples.

2. The biochemical analyzer according to claim 1, including means for reading said indications.

3. The biochemical analyzer according to claim 1 wherein said information is in the form of a magnetic code.

4. The biochemical analyzer according to claim 1, wherein the detection means is located at a predetermined basic position and includes encoder means for generating a plurality of pulses corresponding to said information, said control means controlling said conveying means in response to the number of said pulses generated by said encoder means.

5. The biochemical analyzer according to claim 1, wherein said information is in the form of a punch code.

6. The biochemical analyzer according to claim 1, wherein said information is in the form of a bar code.

* * * * *